United States Patent
Zhao

(10) Patent No.: US 9,089,302 B2
(45) Date of Patent: Jul. 28, 2015

(54) LOCKING MECHANISM FOR PROBE CONNECTOR AND PORTABLE ULTRASOUND DEVICE HAVING THE SAME

(71) Applicant: GE MEDICAL SYSTEMS GLOBAL TECHNOLOGY COMPANY, LLC, Waukesha, WI (US)

(72) Inventor: Zhensong Zhao, Wuxi (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 14/276,233

(22) Filed: May 13, 2014

(65) Prior Publication Data

US 2014/0249421 A1 Sep. 4, 2014

Related U.S. Application Data

(62) Division of application No. 12/759,146, filed on Apr. 13, 2010, now Pat. No. 8,753,280.

(30) Foreign Application Priority Data

Apr. 14, 2009 (CN) .......................... 2009 1 0132729

(51) Int. Cl.
*A61B 8/00* (2006.01)

(52) U.S. Cl.
CPC ................. *A61B 8/4411* (2013.01); *A61B 8/00* (2013.01); *A61B 8/4427* (2013.01); *A61B 8/4455* (2013.01); *A61B 2560/0431* (2013.01)

(58) Field of Classification Search
CPC ........ A61B 8/12; A61B 8/445; A61B 8/4461; A61B 8/06; A61B 8/0858; A61B 8/463
See application file for complete search history.

(56) References Cited

U.S. PATENT DOCUMENTS

| | | | |
|---|---|---|---|
| 5,368,496 A | 11/1994 | Ranalletta et al. | |
| 5,542,425 A | 8/1996 | Marshall et al. | |
| 5,615,682 A | 4/1997 | Stratz, Sr. | |
| 5,820,549 A | 10/1998 | Marian, Jr. | |
| 5,846,097 A | 12/1998 | Marian, Jr. | |
| 5,913,853 A | 6/1999 | Loeb et al. | |
| 5,957,850 A | 9/1999 | Marian, Jr. et al. | |
| 6,695,640 B2 | 2/2004 | Uchibori et al. | |
| 6,790,187 B2 | 9/2004 | Thompson et al. | |
| 6,821,250 B2 | 11/2004 | Mesaros et al. | |
| 2001/0023318 A1 | 9/2001 | Miyaki | |
| 2009/0227874 A1 | 9/2009 | Suri et al. | |
| 2010/0262010 A1 * | 10/2010 | Zhao ............................ | 600/459 |

FOREIGN PATENT DOCUMENTS

KR 20050065910 A 6/2005

* cited by examiner

*Primary Examiner* — Unsu Jung
*Assistant Examiner* — Joel Lamprecht
(74) *Attorney, Agent, or Firm* — Armstrong Teasdale LLP

(57) ABSTRACT

A locking mechanism for probe connector that is connected to a shaft of the probe connector, includes a door and a drive assembly for releasing or locking the probe connector by opening and closing of the door.

17 Claims, 5 Drawing Sheets

LOCKING MECHANISM FOR PROBE CONNECTOR AND PORTABLE ULTRASOUND DEVICE HAVING THE SAME

CROSS REFERENCE TO RELATED APPLICATIONS

This application is a divisional of U.S. patent application Ser. No. 12/759,146 filed Apr. 13, 2010, which claims the benefit of Chinese Patent Application No. 200910132729.3 filed Apr. 14, 2009, both of which are hereby incorporated by reference in their entirety.

BACKGROUND OF THE INVENTION

The present application generally relates to a portable/desktop ultrasound medical diagnostic imaging device, in particular, to a locking mechanism for probe connector and a portable ultrasonic device having the same.

At present, the portable/desktop ultrasound diagnostic imaging device is more and more widely used in clinical and hospital. It is not only used in some traditional medical fields, such as abdomen examination, cardiac examination, and gynecologial and obstetric examination, but also becomes to extend into many new applications, such as helping to diagnose patient visceral injury condition in emergency room or ambulance and helping surgeon to perform a vein puncture operation in operating room.

The portable ultrasound device is just one of portable ultrasound medical diagnostic imaging devices. The portable ultrasound device comprises a probe and a probe connector. The probe is used for transmitting and receiving an ultrasound signal to and from the interior of a human body, which ultrasound signal is then input into the ultrasound device for signal processing and medical imaging. The probe is connected to the ultrasound device by means of the probe connector. Normally because of the limit of space, one portable ultrasound master device is only configured with one female probe connector, and the probe end is provided with a male probe connector (Of course, the primary device may also be provided with a male probe connector, and the probe end is provided with a female probe connector.). The female probe connector on the primary device can be connected each time with a probe by means of the male probe connector at the probe end. Because one probe normally can be used in one or several applications, for example the abdomen probe is normally used for imaging of internal organ of the abdomen, while the superficial probe is used for imaging of superficial blood vessels, the user must replace the different types of probes for different applications when in use of this type of portable ultrasound device. Besides, it needs to lock the male probe connector tightly on the female probe connector to ensure a stable and reliable electrical connection to obtain the optimal image when in replacement of the probe.

In the prior art, normally the female probe connector is provided with a square shaft rotatable to drive a grab within the female connector to rotate and the connection terminal to project/retract. In the locking mechanism in the prior art that locks the male probe connector to a female probe connector, normally the square shaft is provided thereon with a dialing lever and a dialing knob. When the male probe connector at the probe end is connected in place, the dialing lever and the square shaft are driven to rotate by dialing the dialing knob to rotate to lock tight the inner grab and project the connector terminal of the connector, thereby locking the male and female probe connectors and ensuring good electrical connection, or vice versa, releasing the male and female probe connectors.

Such locking mechanism can satisfy the conventional application requirements. In new application fields, however, such structure causes the probe connector to be exposed to outside environments such as operation and to be prone to contamination of blood splash and external environments.

In addition, in emergency treatment or operation, frequent replacement of probes is very time-consuming and tedious. Especially for emergency situations such as emergent operation, each second may be a matter of life of the patient.

BRIEF DESCRIPTION OF THE INVENTION

Embodiments of the invention provide a locking mechanism for probe connector having a protective effect and a portable ultrasound device having the same.

In some embodiments, the locking mechanism is for use with a probe connector, connected to a shaft of the probe connector, comprising a door and a drive assembly for releasing or locking the probe connector by opening and closing of the door.

In one aspect of the drive assembly, the drive assembly comprises a first straight gear, a second straight gear, a first bevel gear and a second bevel gear sequentially connected and a spring located below the first straight gear and being capable of providing torque for the first straight gear.

In some embodiments, the door and the first straight gear are coaxial and have definite relative movement therebetween.

In addition, the spring may be a torsion spring.

In another aspect of the drive assembly, the drive assembly comprises a third straight gear arranged within the door and a fourth straight gear arranged on the shaft.

Further, the door may comprise a door locker and a latch.

Correspondingly, the technical solution of the portable ultrasound device includes a primary system, a female probe connector and a male probe connector as well as a probe mounted on the primary system, and further comprises a locking mechanism for probe connector, the locking mechanism for probe connector comprising a door and a drive assembly for releasing or locking the probe connector by opening and closing of the door.

In one aspect of the drive assembly, the drive assembly comprises a first straight gear, a second straight gear, a first bevel gear and a second bevel gear sequentially connected and a spring located below the first straight gear and being capable of providing torque for the first straight gear.

In some embodiments, the second bevel gear of the locking mechanism for probe connector is connected to the shaft of the male probe connector, and the male probe connector is positioned within the door.

The door and the first straight gear are coaxial and have definite relative movement therebetween.

Further, the spring may be a torsion spring.

In another aspect of the drive assembly, the drive assembly comprises a third straight gear arranged within the door and a fourth straight gear arranged on the shaft.

Further, the male probe connector may comprise two or more male probe connectors.

The door may comprise a plurality of doors.

Compared with the prior art, the locking mechanism for probe connector and the portable ultrasound device having the locking mechanism according to the present invention have at least the following beneficial effects.

First, the locking mechanism for probe connector of this invention has a door to protect the probe connector within the door, namely isolating the probe connector from the external environments, thereby preventing the probe connector from being contaminated by blood splash and external environments, thus performing the function of protection.

Second, since this invention adopts a door, the user only needs to press down the switch of the door in replacement of the probe to realize the actions of opening the door and releasing the probe simultaneously to facilitate replacing of the probe, thereby saving the replacing time and operating action so that the portable ultrasound device of this invention can be applied in wider and finer fields.

Further, the portable ultrasound device of this invention may have two or more male probe connectors. Normally, two or more male probe connectors can satisfy most of the application requirements. Therefore, to use the portable ultrasonic device of this invention can reduce probe replacement operations and save operation and treatment time to the maximum extent.

BRIEF DESCRIPTION OF THE DRAWINGS

In order to understand the content of this invention more completely, description will be made hereinafter with reference to the appended drawings, wherein.

DETAILED DESCRIPTION OF THE INVENTION

Now, embodiments of this invention will be described in details, but this invention is not limited to the following embodiments.

Figure 1:
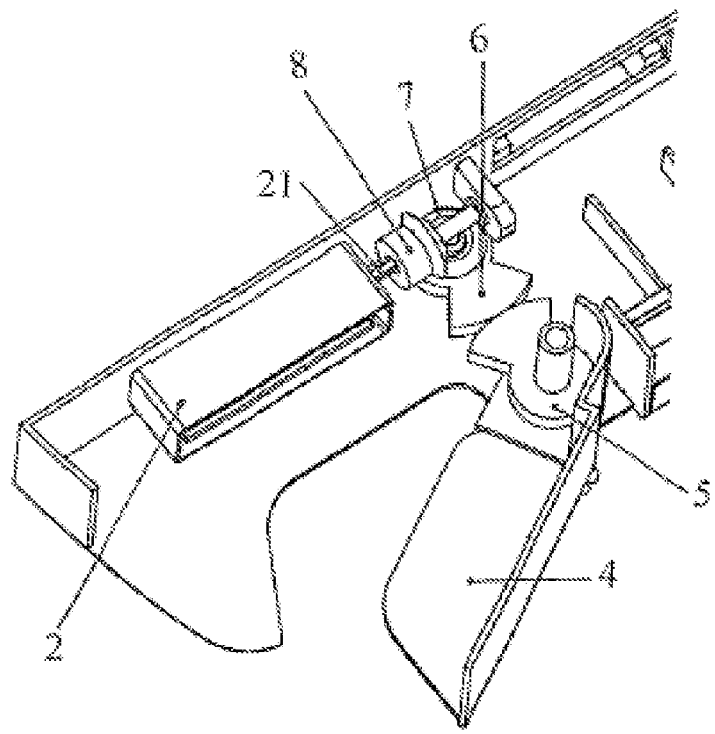
FIG. 1 is a schematic view of one embodiment of the locking mechanism for probe connector of this invention.

As shown in FIG. 1, one embodiment of a locking mechanism for probe connector of this invention is described. The probe connector comprises a female probe connector 2 (see FIG. 3) and a male probe connector 1 (see FIG. 3), wherein the female probe connector 2 (see FIG. 3) is located on a primary device, and a shaft 21 thereof is connected to the locking mechanism for the probe connector, which locking mechanism for probe connector comprises a door 4 and a drive assembly for releasing or locking the probe connector by opening and closing of the door 4.

Typically, when the door 4 is opened, the drive assembly may release the male probe connector 1 (see FIG. 3) and the female probe connector 2 (see FIG. 3); and when the door 4 is closed, the drive assembly may lock the male probe connector 1 and the female probe connector 2.

Figure 2:
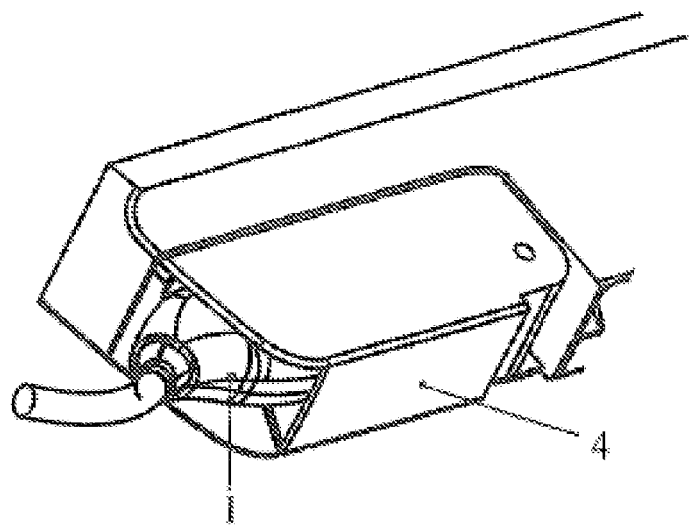
FIG. 2 is spatial view of one embodiment of the locking mechanism for probe connector of this invention with the probe connector locked and the door closed.
Figure 3:
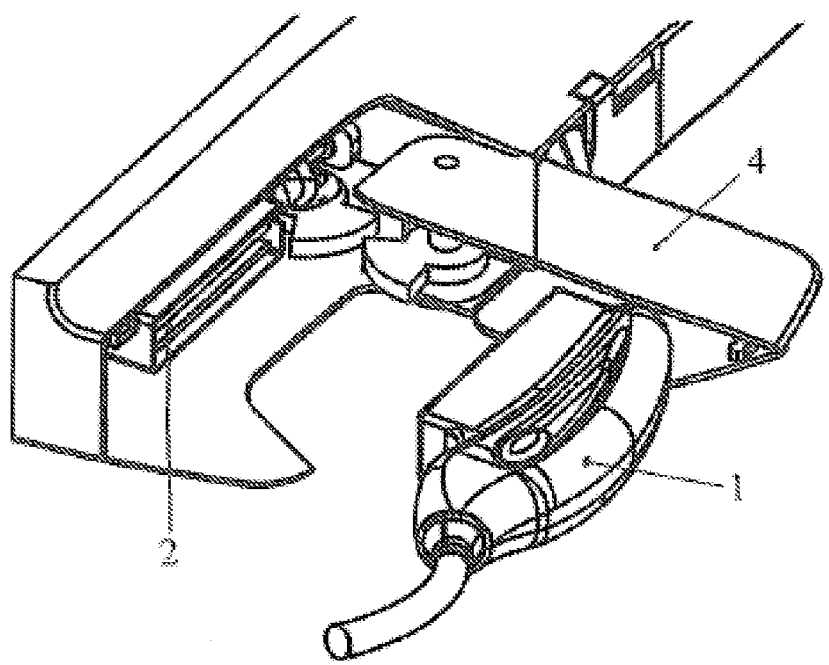
FIG. 3 is spatial view of one embodiment of the locking mechanism for probe connector of this invention with the probe connector released and the door opened.

As shown in FIGS. 2 and 3, they are respectively a spatial view in which the probe connector is locked and the door is closed and a spatial view in which the probe connector is released and the door is opened. It can be seen from FIG. 2 that when the door 4 is closed, the male probe connector 1 and the female probe connector 2 are in a locked status and are protected within the door 4, thereby protecting the probe connector against contamination from blood splash and external environments. In addition, it is possible to enable the edge of the door 4 to tightly fit the profile of the probe and to provide a well-known sealing means therebetween, such as a seal strip, thereby realizing high grade protection, such as waterproof and dustproof. In the status as shown in FIG. 3, the door 4 is opened with the female probe connector 2 and the male probe connector 1 released, thus the user can replace the probe conveniently.

It can be seen from FIG. 1 that the drive assembly comprises a first straight gear 5, a second straight gear 6, a first bevel gear 7 and a second bevel gear 8 sequentially connected and a spring 9 (see FIG. 5) located below the first straight gear 5 with one end connected to the door 4 and another end connected to the first straight gear 5 and being capable of providing torque for the first straight gear, wherein the second bevel gear 8 of the locking mechanism for probe connector is connected to a shaft 21 of the female probe connector 2, and the shaft 21 may be a square shaft.

Further, the first straight gear 5 is fixed at one end of the door 4, and no relative movement exists therebetween. That is, the door 4 and the first straight gear 5 are coaxial and have definite relative movement therebetween. The first straight gear 5 matches with the second straight gear 6. The second straight gear 6 then is fixed together with the first bevel gear 7; hence, the second straight gear 6 and the first bevel gear 7 do not have relative movement therebetween. The first bevel gear 7 matches with the second bevel gear 8.

When it needs to replace the probe, the user opens the door 4, and the spring 9 springs back and pushes the first straight gear 5 to rotate. Because the engagement between the first straight gear 5 and the second straight gear 6, the second straight gear 6 is also driven to rotate, thereby causing first bevel gear 7 to rotate. Because the engagement between the first bevel gear 7 and the second bevel gear 8, the first bevel gear 7 drives the second bevel gear 8 to rotate. The shaft 21 of the female probe connector 2 is rotated with the second bevel gear 8.

Because the teeth numbers of the gears 5, 6, 7 and 8 may be the same, so they translate the same rotation angle. When the door opens 60 degrees, the first straight gear 5, the second straight gear 6 and the first bevel gear 7 and the second bevel gear 8 all rotate 60 degrees. So the shaft 21 rotates 60 degrees and releases the probe. In this specific embodiment, the spring 9 then reaches the spring back limit and finishes giving the torque. User can take away the probe, or open the door to 90 degrees or more manually for taking away the probe more easily. In this specific embodiment, in the space more than 60 degrees, no gear engagement will work.

Although this embodiment provides the case that the spring back limit of the spring 9 can open the door 4 to 60 degrees, those skilled in the art can certainly use other spring back limits to open the door 4 to different degrees as long as the rotation space is enough for taking away the probe. Likewise, the teeth numbers of the gears 5, 6, 7 and 8 may also be different such that it is possible to obtain different movement angles and to change the force needed in opening and closing of the door.

After the probe is replaced, it only needs to close the door 4. The closing force of the door 4 overcomes the torque of the spring 9 and compresses the spring 9. With the door closing, the gear will engage and rotate in the opposite direction of door opening process. The shaft 21 will lock the probe after finishing the 60 degree rotation driven by the gear set. The action of closing the door is finished.

Figure 5:
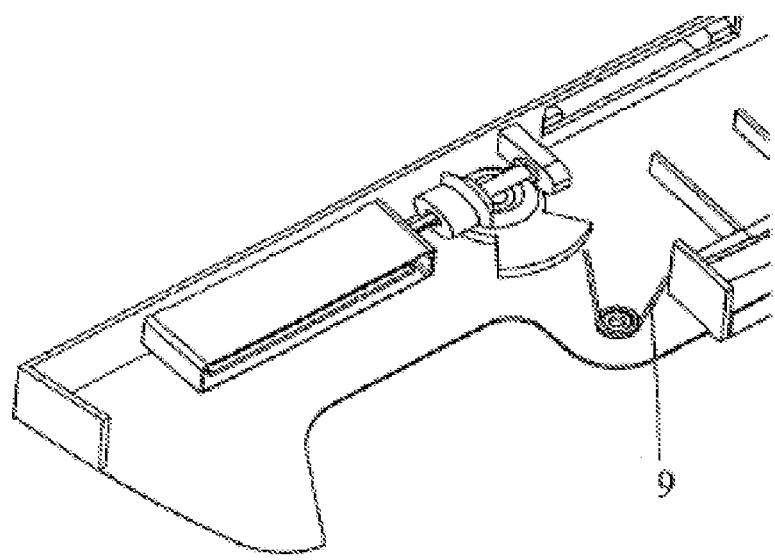
FIG. 5 is a schematic view of the spring in the locking mechanism for probe connector of this invention.

Also shown in FIG. 5, the spring 9 may be a torsion spring.

Figure 6:
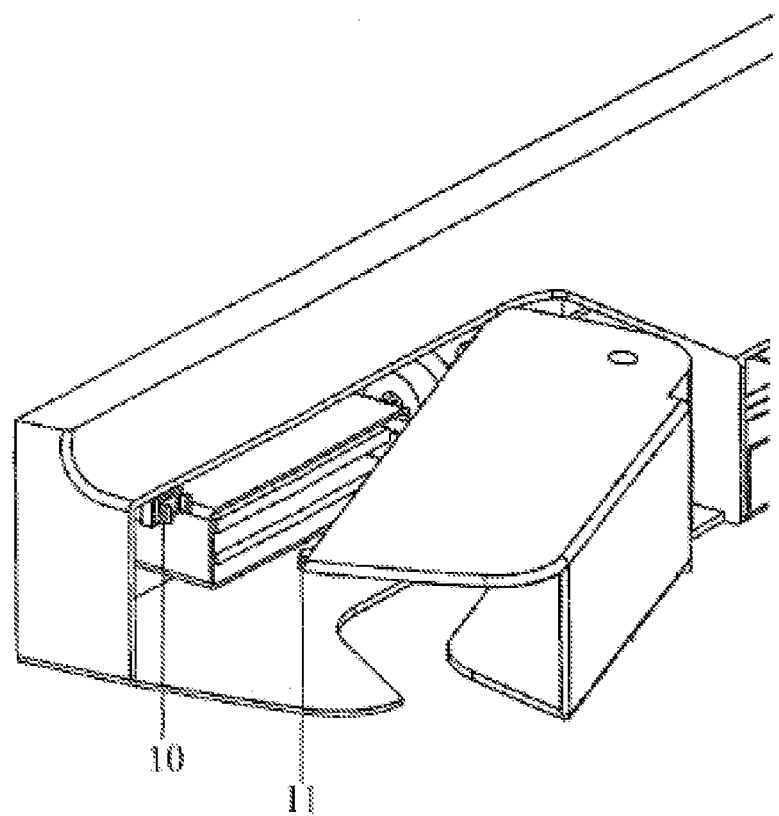
FIG. 6 is a spatial view showing the positions of the door locker and the latch.
Figure 7A:
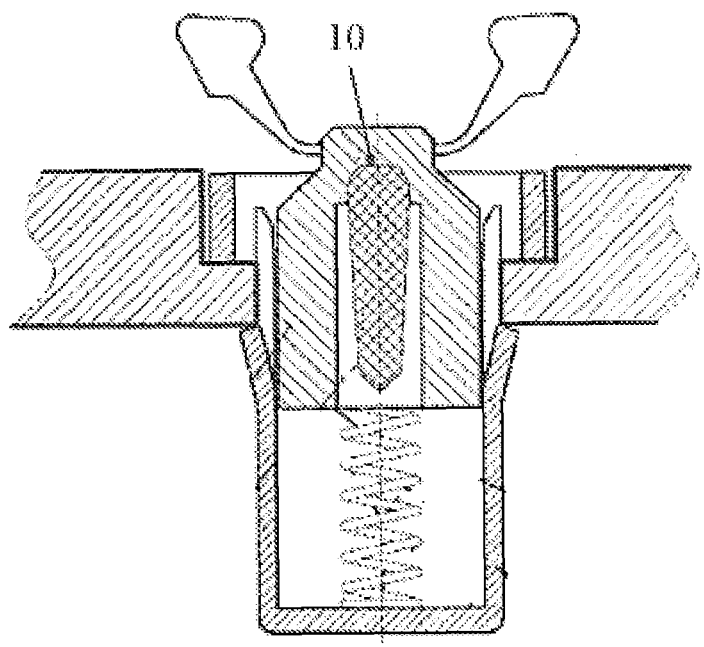
FIG. 7A is a half-section view showing the door locker.
Figure 7B:
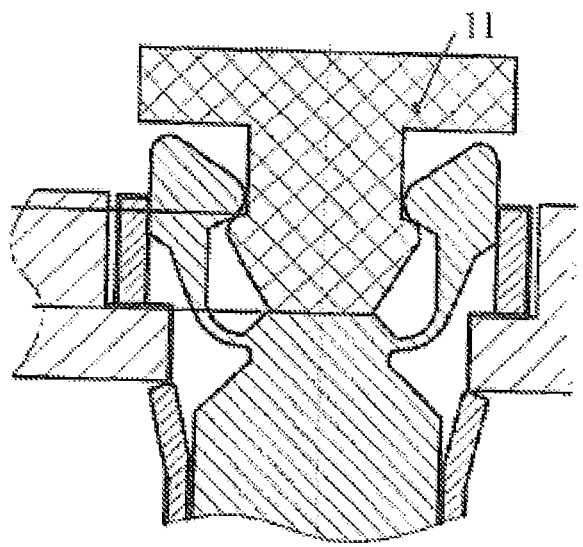
FIG. 7B is a half-section view showing the latch.

As shown in FIG. 6 and FIGS. 7A and 7B, the door 4 may comprise a locker 10 and a latch 11. The door 4 may be an automatic door. The pair of door locker 10 and latch 11, normally used in some drawers or small doors on electrical device, is well-known technology. Under the lock status, the latch 11 will exit from the locker 10 when the latch is pushed against, thereby opening the door 4. Under the open status of the door, the latch 11 can be pushed into the locker 10 when the latch 11 is pushed against, thereby locking the door, namely closing the door. Use of this pair of parts on the door 4 is enough to let the action simple enough. The user just needs to push against the door, the door 4 will open automatically.

Figure 8:
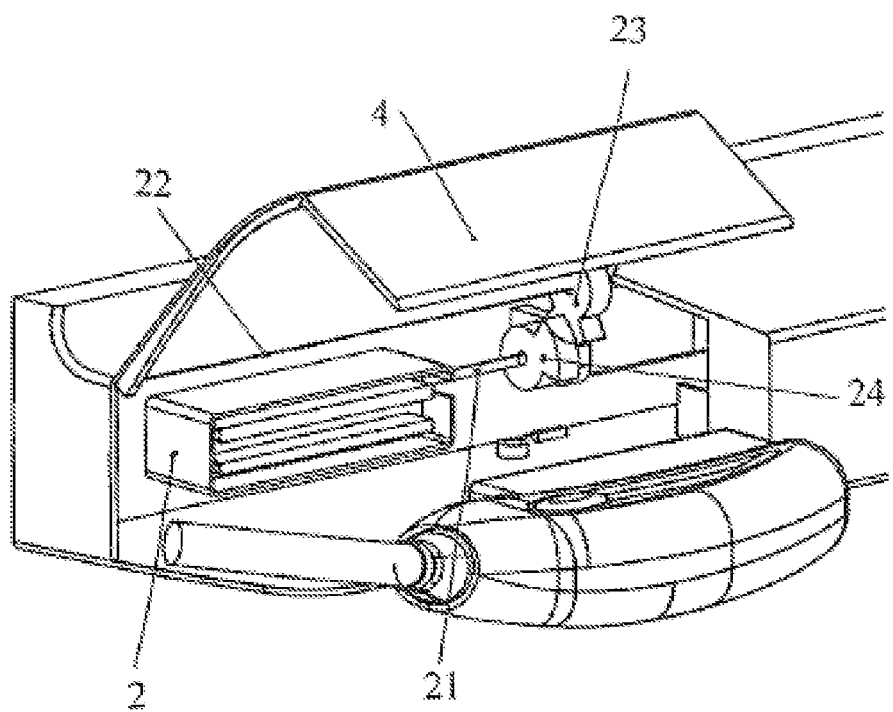
FIG. 8 is a schematic view of another embodiment of the locking mechanism for probe connector of this invention.

As another embodiment of this invention, shown in FIG. 8, the drive assembly comprises a third straight gear 23 arranged within the door 4 and a fourth straight gear 24 arranged on the square shaft 21. The door 4 may rotate about a rotation shaft 22 which may be located on the top of the door 4. When the door 4 rolls over upward, the door is in the open status. The third straight gear 23 arranged within the door 4 is engaged with the fourth straight gear 24 arranged on the square shaft. These two matching gears rotate in opposite directions, thereby realizing downward rotation of the square shaft 21 to release the male probe connector and the female probe connector, or vice versa, to lock the male probe connector and the female probe connector.

Certainly, it also possible to make any modification, variation and substitution to the drive assembly. For example, if the bottom space allows, it is also feasible to provide a square hole within the door 4 for matching with the square shaft 21 and set the rotation shaft 22 of the door 4 coaxial with the central axis of the square shaft 21, thereby directly realizing locking and releasing of the male probe connector by rolling over of the door 4. Seeing that this structure is similar to the foregoing two embodiments and are simple, no further description will be given herein.

In the foregoing embodiments, downward rotation of the square shaft 21 of the male probe connector 2 is for releasing, while the upward rotation of the square shaft 21 is for locking. Of course, it possible to adjust the rotation direction of the square shaft. Correspondingly, it is possible to adjust matching relation of the gear set to achieve the desired purpose of opening the door to release and closing the door to lock. This is easy for those skilled in the art to get familiar, and thus no further description will be given herein.

This invention has further disclosed a portable ultrasound device comprising a primary system, a female probe connector 2 connected to the primary system as well as a male probe connector 1 and a probe, and further comprising a locking mechanism comprising a door 4 and a drive assembly for releasing or locking the probe connector by opening and closing of the door 4.

The primary system is the main portion of the portable ultrasound device and which can use any technology well known to those skilled in the art.

In one embodiment, the drive assembly comprises a first straight gear 5, a second straight gear 6, a first bevel gear 7 and a second bevel gear 8 sequentially connected and a spring 9 located below the first straight gear 5 and being capable of providing torque for the first straight gear.

Wherein the second bevel gear 8 of the locking mechanism of a probe connector is connected to the shaft of the female probe connector, and the male probe connector 1 is positioned within the door 4.

Further, the door 4 and the first straight gear 5 are coaxial and have definite relative movement therebetween. The spring 9 may be a torsion spring.

In another embodiment, the drive assembly comprises a third straight gear 23 arranged within the door 4 and a fourth straight gear 24 arranged on the shaft 21. The door 4 may rotate about the rotation shaft 22 which may be located on the top of the door 4. When the door rolls over upward, the door is in an open status. Within the door 4 is arranged a third straight gear 23 which engages with the fourth straight gear 24 on the square shaft. These two matching gears rotate in opposite directions, thereby releasing downward rotation of the square shaft 21 to release the male probe connector and the female probe connector a, or vice versa, to lock the male probe connector and the female probe connector.

Figure 4:
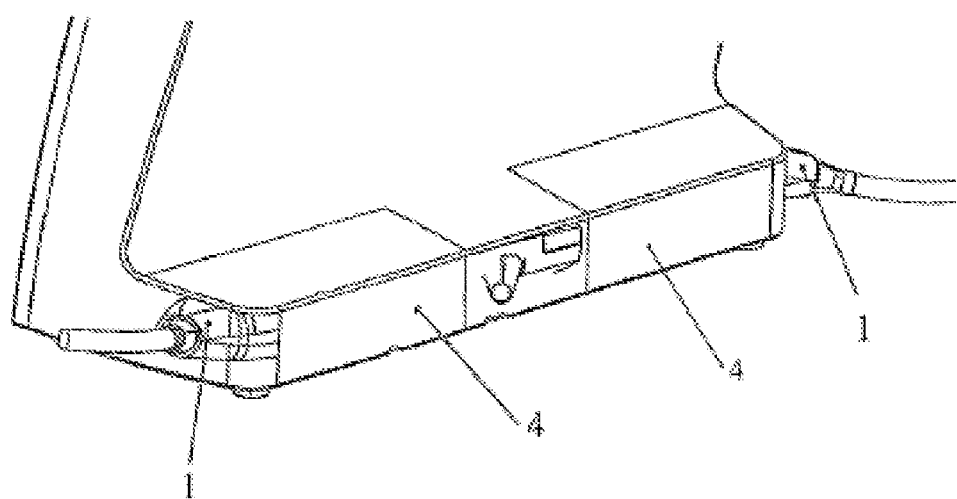
FIG. 4 is a partial spatial view of the portable ultrasound device having a plurality of probe connectors.

Shown in FIG. 4 is a partial spatial drawing of the portable ultrasound device with a plurality of probe connectors. This device comprises two or more female probe connectors (not shown) for locking with or releasing from the male probe connectors 1 simultaneously to connect a plurality of probes. Normally, three probes can satisfy most of the application requirements. Each female probe connector is provided outside with a door 4 and a drive assembly for releasing or locking the probe connector by opening and closing of the door.

The locking mechanism for probe connector of this invention can be used in any portable ultrasound device.

Although the specific embodiment of this invention have described above with reference to the appended drawings, those skilled in the art can make various modifications, variations and equivalent substitutions to the invention without departing from the spring and scope of this invention. These variations, modifications and equivalent substitutions all intend to fall within the spirit and scope defined by the appended claims.

What is claimed is:

1. A locking mechanism for use with a portable ultrasound probe connector connected to a shaft of the ultrasound probe connector, the locking mechanism comprising a door and a drive assembly configured to selectively release and lock the probe connector by opening and closing the door, the drive assembly comprising a first straight gear arranged within the door and a second straight gear arranged on the shaft.

2. The locking mechanism according to claim 1, wherein the door comprises a door locker and a latch.

3. The locking mechanism according to claim 1, wherein the shaft is a square shaft.

4. The locking mechanism according to claim 1, wherein the probe connector comprises a plurality of probe connectors.

5. The locking mechanism according to claim 1, wherein the door comprises a plurality of doors.

6. A portable ultrasound device comprising:
a primary system;
a female probe connector mounted on the primary system;
a male probe connector;
a probe; and
a locking mechanism coupled to the male probe connector, the locking mechanism comprising a door and a drive assembly configured to release and lock the male probe connector to the female probe connector by opening and closing the door, wherein the female probe connector comprises a shaft, and the drive assembly comprises a first straight gear arranged within the door and a second straight gear arranged on the shaft.

7. The portable ultrasound device according to claim 6, wherein the door comprises a door locker and a latch.

8. The portable ultrasound device according to claim 6, wherein the female probe connector comprises a plurality of female probe connectors.

9. The portable ultrasound device according to claim 6, wherein the male probe connector comprises a plurality of male probe connectors.

10. The portable ultrasound device according to claim 6, wherein the door comprises a plurality of doors.

11. The portable ultrasound device according to claim 6, wherein the shaft is a square shaft.

12. An ultrasound device comprising:
   a female probe connector;
   a male probe connector sized to be inserted into the female probe connector; and
   a locking mechanism coupled to the male probe connector and the female probe connector, the locking mechanism comprising a door and a drive assembly configured to lock the male probe connector in an inserted position within the female probe connector and to release the male probe connector from the female probe connector, wherein the female probe connector comprises a shaft, and wherein the drive assembly comprises a first straight gear arranged within the door and a second straight gear arranged on the shaft.

13. The ultrasound device according to claim 12, wherein the door comprises a door locker and a latch.

14. The ultrasound device according to claim 12, wherein the female probe connector comprises a plurality of female probe connectors.

15. The ultrasound device according to claim 12, wherein the male probe connector comprises a plurality of male probe connectors.

16. The ultrasound device according to claim 12, wherein the door comprises a plurality of doors.

17. The ultrasound device according to claim 12, wherein the shaft is a square shaft.

\* \* \* \* \*